(12) United States Patent
Daikuzono (10) Patent No.: US 6,679,837 B2
(45) Date of Patent: Jan. 20, 2004

(54) LASER LIGHT IRRADIATION APPARATUS (75) Inventor: Norio Daikuzono, Napa, CA (US)

(73) Assignee: Intlas Ltd., Maineville, OH (US)

( * ) Notice: Subject to any disclaimer, the term of this patent is extended or adjusted under 35 U.S.C. 154(b) by 0 days.

(21) Appl. No.: 09/870,991

(22) Filed: Jun. 1, 2001

(65) Prior Publication Data

US 2002/0183727 A1 Dec. 5, 2002

(51) Int. Cl.[7] .............................................. A61B 1/015
(52) U.S. Cl. ........................ 600/157; 600/160; 606/10
(58) Field of Search ....................... 606/10–16; 607/89; 600/108, 157, 160

(56) References Cited

U.S. PATENT DOCUMENTS

| 4,281,646 | A | * | 8/1981 | Kinoshita | .................... | 600/157 |
| 4,844,052 | A | * | 7/1989 | Iwakoshi et al. | ........... | 600/157 |
| 5,207,213 | A | * | 5/1993 | Auhll et al. | ................. | 600/104 |
| 5,419,309 | A | * | 5/1995 | Biehl | ......................... | 600/187 |
| 5,518,502 | A | * | 5/1996 | Kaplan et al. | .............. | 600/157 |
| 5,634,790 | A | * | 6/1997 | Pathmanabhan et al. | .... | 600/160 |
| 5,860,967 | A | * | 1/1999 | Zavislan et al. | .............. | 606/10 |
| 6,203,540 | B1 | * | 3/2001 | Weber | ......................... | 604/22 |
| 6,270,342 | B1 | * | 8/2001 | Neuberger et al. | .......... | 433/132 |
| 2002/0007109 | A1 | * | 1/2002 | Gminder et al. | ............ | 600/157 |

* cited by examiner

Primary Examiner—Roy D. Gibson
Assistant Examiner—Henry M. Johnson
(74) Attorney, Agent, or Firm—McDermott, Will & Emery (57) ABSTRACT The present invention provides a medical surgical or dental laser light irradiating apparatus which enables operators as well as third persons to precisely view the treatment. The medical laser light irradiating apparatus of the present invention comprises an optical fiber 3 for emitting from its front end the laser light which is incident upon the rear end thereof from said laser light supply means, a handpiece 1 for holding said optical fiber 3, an light incident face 21 which is made integrally with said handpiece 1 so that it faces at least a laser light irradiated area, imaging means 20 for imaging of at least laser light irradiated area based upon the light which is received through the light incident face 21, display means 30 for displaying a result of imaging from said imaging means 20, and jetting means 40, 40A, 41, 42 for jetting an air to an area in front of said light incident face 21.

7 Claims, 8 Drawing Sheets

Fig. 7

LASER LIGHT IRRADIATION APPARATUS

TECHNICAL FIELD TO WHICH THE INVENTION BELONGS

The present invention relates to a laser light irradiation apparatus for surgery and dentistry, and in particular to a laser light irradiation apparatus, excluding endoscopic surgery apparatus, which is preferable for surgery and dentistry and provides various advantages by imaging the treatment conditions with imaging means which is integral with a handpiece.

BACKGROUND OF THE INVENTION

Various many medical laser irradiating apparatuses such as laser mess for surgery have heretofore been known. They have been recently used for the dentistry. For example, irradiation of the caries tooth with pulsed laser light is disclosed in U.S. Pat. No. 4,818,230.

However, the treatment with prior art medical laser light irradiating apparatus has a problem that it is difficult for persons other than an operator to observe the conditions of a part which is being irradiated with the laser light.

BACKGROUND OF THE INVENTION

Various many medical laser light irradiating apparatuses such as laser mess for surgery have heretofore been known. They have been recently used for the dentistry. For example, irradiation of the caries tooth with pulsed laser light is disclosed in U.S. Pat. No. 4,818,230.

However, the treatment with prior art medical laser light irradiating apparatus has a problem that it is difficult for persons other than an operator to view the situation of a part which is being irradiated with the laser light. Accordingly, it is very difficult for third person such as assistants and advisers to observe the treatment conditions in a precise manner for giving appropriate advice to the operator.

Even the operator himself or herself may not readily observe the treatment conditions depending upon the treatment position.

Therefore, it is a main object of the present invention to provide a medical laser light treatment apparatus which enables even the operator as well as third persons to precisely observe the treatment conditions on treatment.

SUMMARY OF THE INVENTION

In accordance with the present invention, there is provided a laser light irradiating apparatus which uses laser light from laser light supply means for treatment, comprising: an optical fiber for emitting from its front end the laser light which is incident upon the rear end thereof from said laser light supply means; a handpiece for holding said optical fiber; a light incident face which is made integrally with said handpiece so that it faces at least a laser light irradiated area; imaging means for imaging of at least said laser light irradiated area based upon the light which is received through the light incident face; display means for displaying a result of imaging from said imaging means; and jetting means for jetting an air to an area in front of said light incident face.

Since at least the laser light irradiated area is imaged for displaying on a display of an computer and the like during the laser light irradiation when needed in accordance with the present invention, third persons other than a treating person (operator) is capable of observing the conditions of the treated part which is being irradiated with laser light in a precise manner. Accordingly, it is possible for the third person such as assistants and advisers to precisely observe the treatment conditions and give appropriate advice to the treating person. The treating person himself or herself is capable of precisely observing the conditions of the treated site by viewing the display even if the treated cite is complicated.

Since the laser light irradiated area is imaged, the treating conditions can be recorded if the images are recorded by means of known apparatus such as video cassette recorder or computer. The recorded images can be used for confirmation or presentation of the treated conditions to the patient.

Imaging, displaying or recording can be conducted constantly or whenever needed. Imaging can be conducted at least during the irradiation with the laser light by interlocking the imaging with a laser light irradiation switch.

The present invention further comprises means for imaging and displaying the laser light irradiated area as well as jetting mean for jetting an air toward an area in front of the light incident face. When a target tissue is irradiated with laser light, the target issue and the like will usually be evaporated so that fumes rise, or it will be incised or scattered. If the cooling water is sprayed to the laser light irradiated area, it will be scattered. When the fumes or scattered tissue pieces are stuck upon the light incident face, clear imaging of the laser light irradiated area will become impossible. In contrast to this, the present invention makes it possible to blow an air toward an area in front of the light incident face. Blowing air will blow the fumes and scattered tissue pieces to prevent them from reaching at least the light incident face. Therefore, clear imaging of the laser light irradiated area becomes possible.

In the present invention, it is preferable that the jetting of the air with jetting means be continued at least during the irradiation with laser light. This positively prevents the fumes or the scattered tissue pieces due to laser light irradiation from sticking to the light incident face.

It is preferable that the light incident face and imaging means comprise a camera which is integral with said handpiece. In this case, the camera is preferably movable with respect to said handpiece in a longitudinal direction thereof. In this case, mounting means for mounting said movable camera is preferably provided. It is possible to adjust the composition of the images by adjusting the position of the camera with respect to the laser light irradiated area during the treatment, or before or after of the treatment, or when needed.

Since the target tissue or its peripheral tissue will generate some heat when the tissue of the treatment target is irradiated with the laser light, it is necessary to cool it. In accordance with the present invention, there is preferably provided at least one of air supply means for blowing air into a space in front of the front end of said optical fiber and water supply means for supplying water to the front end of said optical fiber; said laser light, said air and said water are emitted to at least the laser light irradiating area.

As one development of the present invention, it is possible to transmit an imaging result to other display devices via a communication network. This enables third persons such as assistants or advisors to precisely observe the treatment conditions in a position remote from the treating site so that they can give appropriate advice from the remote area.

PREFERRED MODES OF EMBODYING THE INVENTION

Now, modes of embodying the invention will be described in more detail with reference to the drawings.

Figure 1:
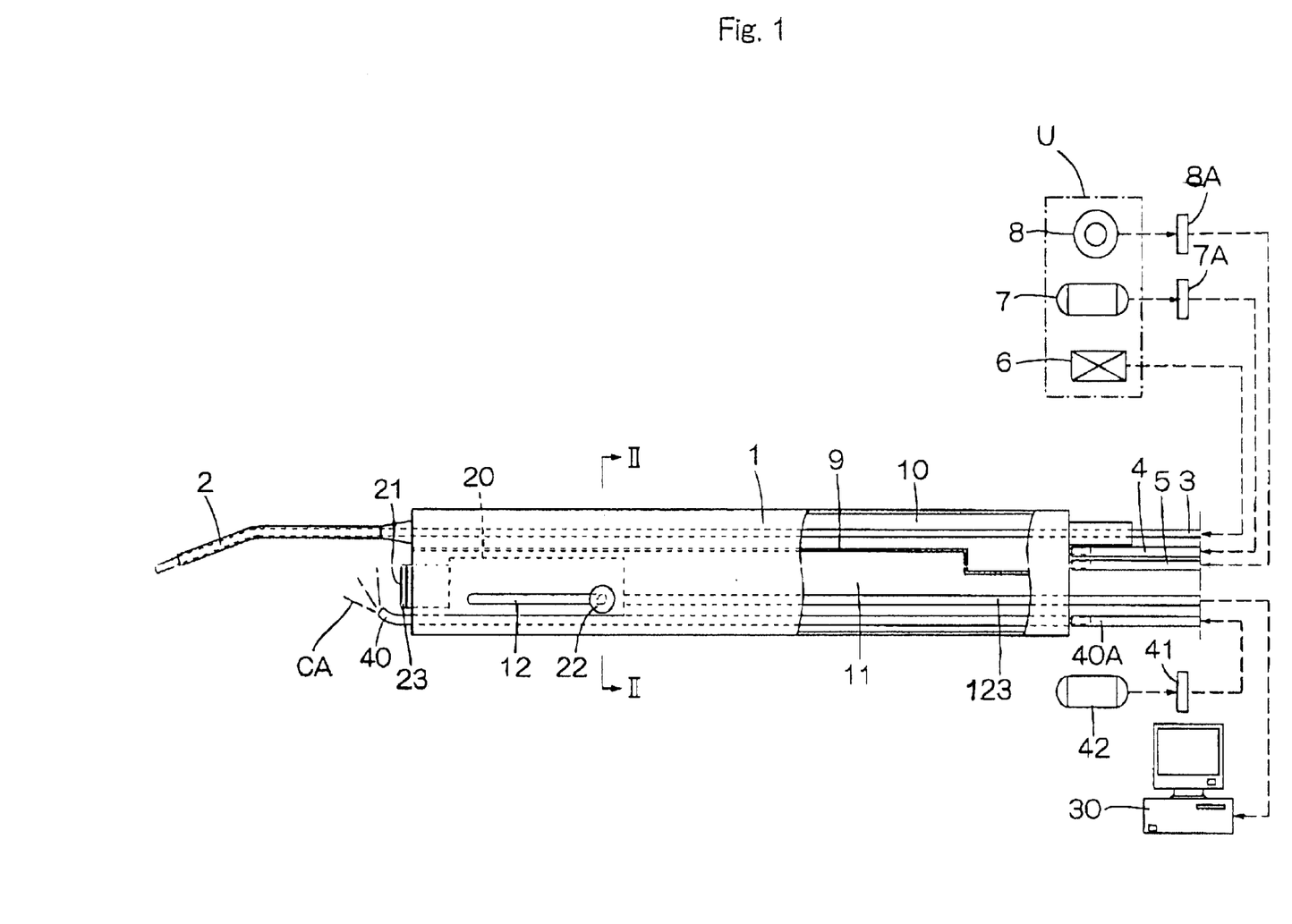
FIG. 1 is an explanatory view of the laser light irradiation apparatus.
Figure 2:
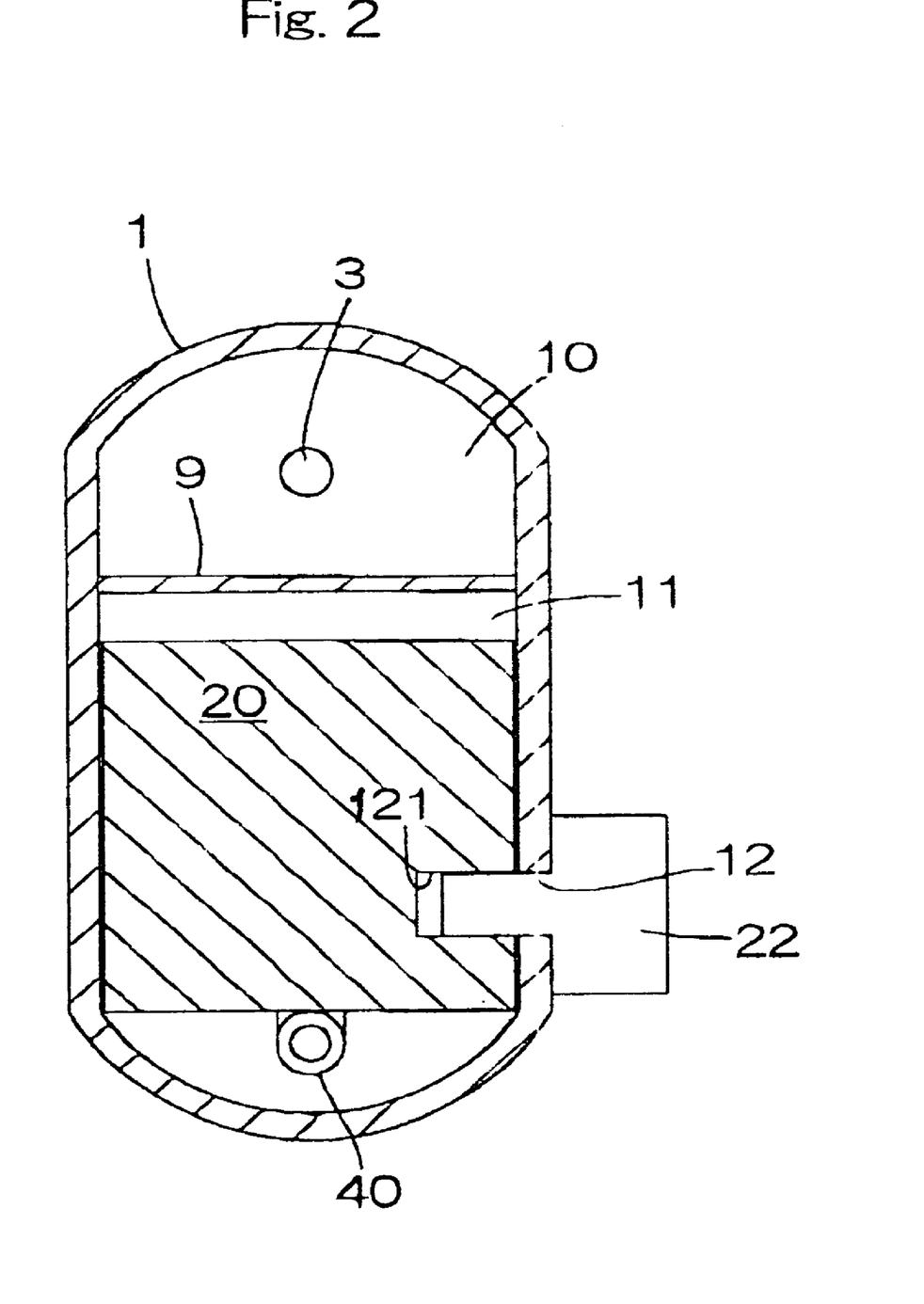
FIG. 2 is an enlarged sectional view taken along the line II—II in FIG. 1.

Referring now to FIGS. 1 and 2, fundamental concept of the invention will be described in detail. An optical fiber 3 is used as laser light transmitting member of the present invention. The laser light from laser light supply means is incident upon the rear end of the optical fiber and is transmitted through the fiber 3 and is emitted from the front end of the fiber and is then incident upon a treatment target area (living tissue as well as artificial organ disposed therein).

Figure 4:
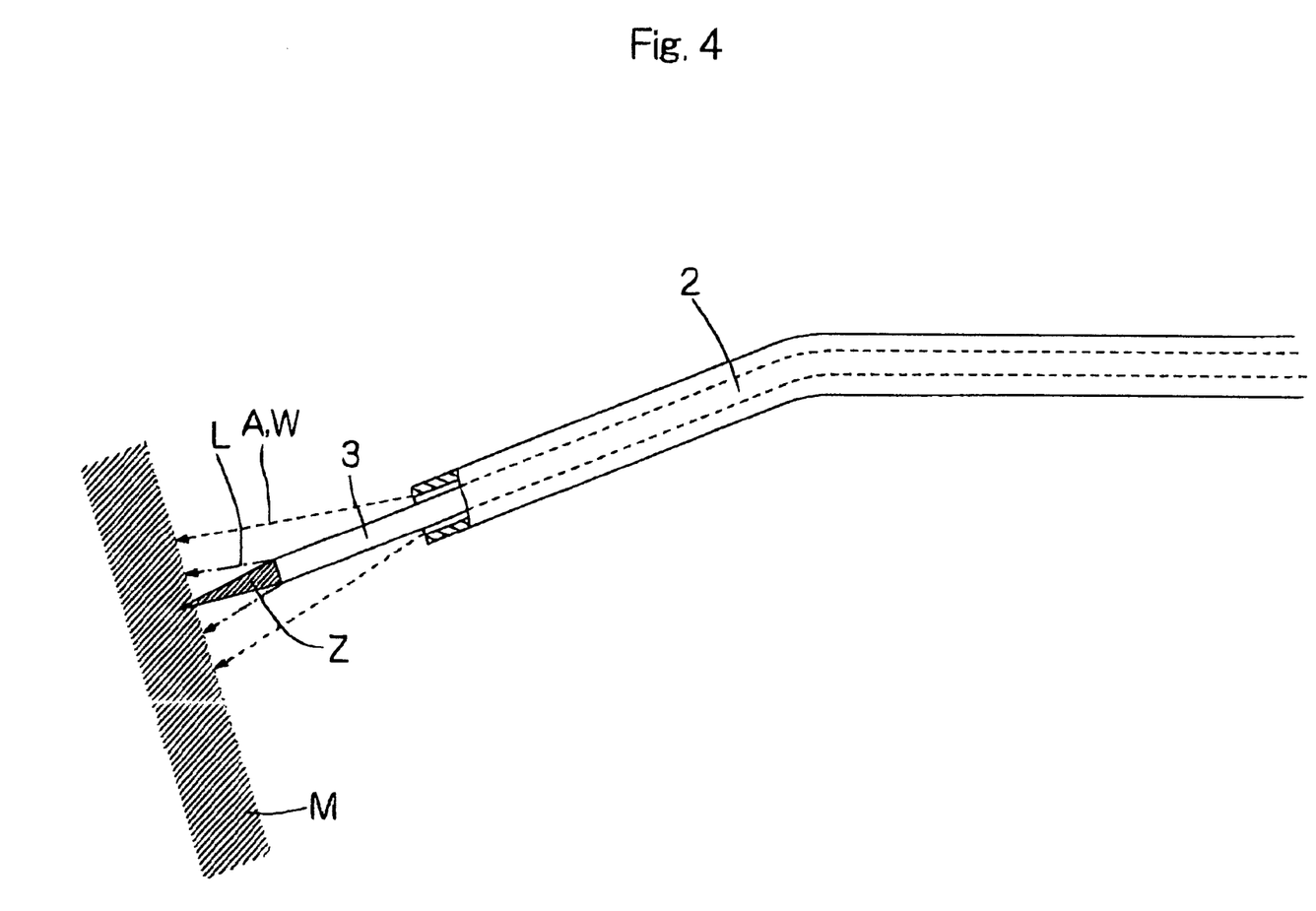
FIG. 4 is an enlarged view showing another embodiment.
Figure 8:
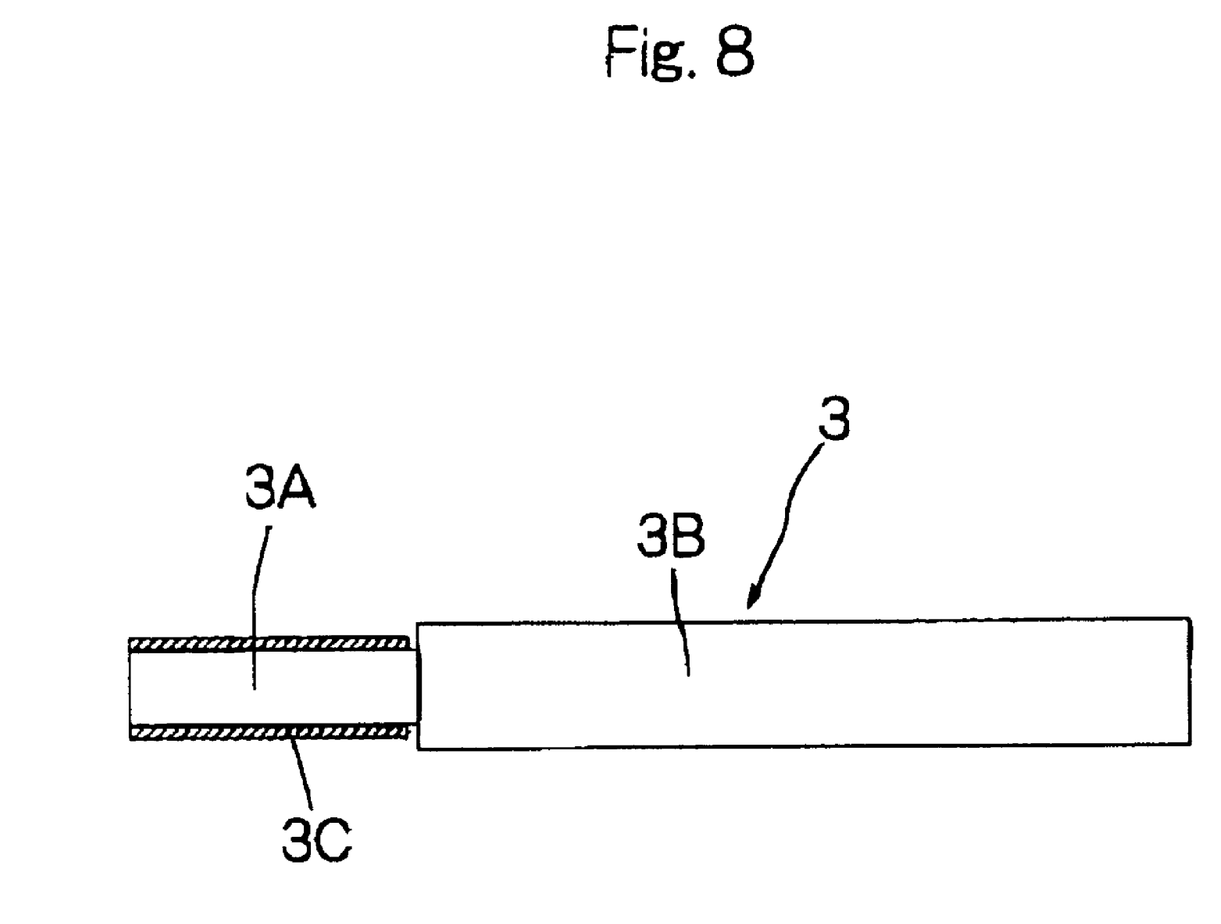
FIG. 8 is a front view showing the form of the front end portion of an optical fiber.

A core 3C of the optical fiber 3 is exposed at the front end of the fiber 3 by removing of a clad 3B as shown in FIG. 8. Since the laser light is emitted from the lateral (peripheral) side of the fiber 3 as well as front end thereof due to the presence of the exposed portion of the core 3C, simple and effective laser treatment can be conducted depending upon the target to be treated. Removal of the clad for exposing the core 3C can be easily accomplished by using a ring cutter and the like. The exposed portion of the core 3C can be formed with a layer 3C having powdery material which absorbs laser light to generate heat. In this case, there is an advantage that the laser light is uniformly emitted from the lateral side of the fiber. The optical fiber 3 may be in the shape of cone or other suitable pointed shape at the front end thereof as shown in FIG. 4.

The optical fiber 3 is held by a handpiece 1. The handpiece 1 is hollow so that it has an inner chamber which is separated into upper and lower chambers 10 and 11 by a diaphragm 9 and has a guide tube 2 at the front end thereof. The guide tube 2 is in communication with the upper chamber 1 of the handpiece 1. The optical fiber 3 extends through the rear guide portion of the handpiece and the upper chamber 10 of the handpiece 1 and the guide tube 2 and extends beyond the front end of the guide tube 2 so that it is exposed.

Figure 3:
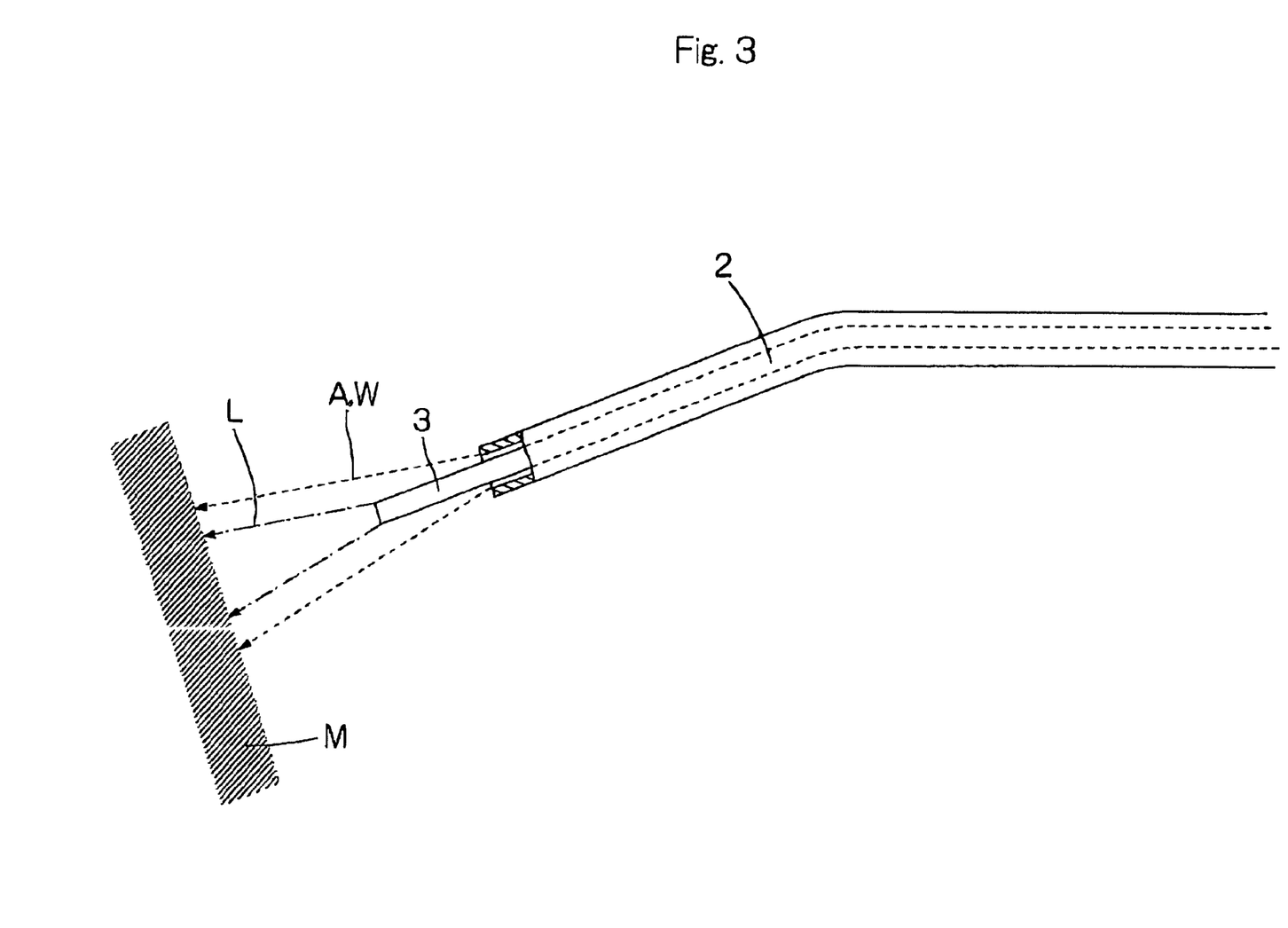
FIG. 3 is an enlarged view.

In the embodiment, a space is formed between the guide tube 2 and the optical fiber 3 as clearly shown in FIG. 3. Air A and/or water W which is fed from the rear of the handpiece 1 through an air supply tube 4 and water supply tube 5 (refer to FIG. 1) which are made of flexible plastics is passed through the upper chamber 10 of the handpiece 1 and is sprayed forwardly toward a target area M in a coaxial manner through the space between the guide tube 2 and optical fiber 3 and over the periphery of the optical fiber 3.

The optical fiber 3, air supply tube 4 and water supply tube 5 can be detachably linked with connecting openings of the laser light irradiating unit U (not shown in detail). The laser light irradiating unit U comprises laser light supply means, that is, laser light generator 6 and a controller for controlling its output (not shown). The laser light irradiating unit U further comprises an air supply compressor 7 and a water supply pump 8.

The laser light irradiating unit U has, for example, a control panel so that the width of one pulse, the energy of one pulse (in unit of mJ), repetition rate of one pulse of the laser light, the amount of the supplied air A per minute, the amount of the supplied air per minute and the amount of the supplied water per minute can be selected and preset by operating the control panel. A foot switch 7A for supplying air and foot switch 8A for supplying water are connected to the laser light irradiating unit U. Selection between air supply and stop mode and water supply and stop mode may be conducted by turning on or off the air supply foot switch 7A and water supply foot switch 8A. Selection between turning on and off of the laser light irradiation can be conducted by means of a switch provided on the handpiece 1 or a foot switch. The kind of the used laser light can be suitably selected depending upon the treatment target.

A camera 20 such as CCD video camera is incorporated in the lower chamber 11 of the handpiece 1 in such a manner that the light incident face 21 thereof faces the front end of the optical fiber 3. It is preferred that a filter 23 which reflects the laser light is mounted on the front face of the lens of the camera 20 as shown in the drawing so that the imaging result is not influenced by the laser light. Although the front face of the filter 23 constitutes light incident face 21 of the present invention in this case, the front face of the lens of the camera 20 constitutes the light incident face 21 when the filter 23 is not used.

In this case, the lower chamber 11 of the handpiece 1 is separated from the upper chamber 10 in an air-tight manner and is formed with an opening (not shown) at the front end wall. The camera 20 can be projected through the opening. As also shown in FIG. 2, the sidewall of the handpiece 1 which corresponds to the lower chamber 11 is formed with an elongated hole 12 which communicated with the inside and outside of the handpiece 1. The elongated hole 12 extends in a longitudinal direction of the handpiece 1.

A screw hole 121 having a diameter less than the width of the elongated hole 12 is formed at the base end of the camera in a position corresponding to the elongated hole 12 of the handpiece 1. A screw member 22 having a head, the diameter of which is larger than that of the elongated hole 12 is screwed into the screw hole 121 of the camera 20 through the elongated hole 12 from the outside of the handpiece 1. Accordingly, the camera 20 is movable over the longitudinal length of the elongated hole 12 when the screw member is slightly loosed. On the other hand, the camera 20 can be secured to the handpiece 1 by tightening of the screw member 22. In such a manner, composition of video images can be adjusted by adjusting the position of the camera 20 with respect to the laser light irradiating area if necessary during and before and after the treatment.

In this case, the camera 20 is connected to a display such as TV or computer 30 via a video image signal transmission cable 123 which extends through the lower chamber 11 of the handpiece 1 and the rear portion thereof to the outside of the handpiece.

A result of image pickup by the camera 20 can be recorded by known recording devices such as video cassette recorders and computers (not shown). Image picking up and display by camera 20 can be constantly conducted while the treating instrument is operating or whenever needed. For example, image picking up can be conducted at least during irradiation with laser light by interlocking the camera with the irradiating switch of the laser light. Image picking up and display by camera 20 can be controlled by the computer 30.

In this case, a jetting tube 40 for eliminating dust on the light incident face 21 is provided below the camera 20. In the illustrated case, the jetting tube 40 is made integrally with the lower side of the camera 20 by means of bonding or welding and is movable in association with the movement of the camera. The jetting opening at the front end of the jetting tube 40 is located in the vicinity of the light incident face 21 of the camera 20 and is opened toward the space in front of the light incident fact 21 (the space between the light incident face 21 and the front end of the optical fiber 3 in the illustrated case). Although not illustrated in detail, the base end portion of the jetting tube 40 is of a double-walled structure or bellows structure so that it is extendable. The jetting tube 40 extend through the lower chamber 11 of the handpiece 1 and is connected to a flexible outer jetting tube 40A at the rear connecting portion of the handpiece 1. The outer jetting tube 40A is connected to an air-jetting compressor 42 via a jetting switch 41. The jetting switch 42 may be common with the actuation switch of the camera, the above-mentioned laser light irradiating switch, air supply foot switch 7A or water supply switch 8A, or alternatively may be interlocked therewith.

On treatment, the image of the laser light irradiated area including the front end portion of the optical fiber 3 is picked up by turning on the camera 20 and is displayed on the display 30 constantly or whenever needed. The target area M is irradiated with laser light as shown in FIG. 3 or 4 by suitably turning on or off the laser light irradiating switch while dust eliminating gas such as air CA is blown to the space in front of the light incident face 21 from the front end of the jetting tube 40 by turning on the jetting switch 41.

Simultaneously, cooling and cleaning of the target area M can be achieved by jetting at least one of the cooling air A and water W upon the target area M constantly or whenever needed by actuating the air supply foot switch 7A and water supply foot switch 8A.

In such a manner, the portion at the target area M, which is irradiated with laser light is subjected to treatment by evaporation, incision and decomposition. The images of treated portion are picked up by the camera and are displayed on the display 30. This display 30 enables persons other than physician (operator) to observe the conditions of the treated portion which is being irradiated with laser light in precise and minute manner. Accordingly, for example, a third person 1 such as assistant or leader can precisely and minutely observe the treatment to give an appropriate advice to the operator. Even the operator himself or herself can precisely and minutely view the treatment through the display 30 even if the treated portion is complicated. A video camera as well as still camera may be used as the camera 20. When the video camera is used, the treated portion can be viewed on a real-time basis. As mentioned above, the image pick-up result may be recorded on an appropriate recording device or transmitted to other display of the computer at the remote area over the communication network such as Internet. In latter case, remote treatment viewing and guidance to the operator can be conducted.

During treatment, fumes may rise due to evaporation of the tissue, and the target tissue may be incised or scattered. When the cooling water W is sprayed upon the laser light irradiated area, it will be scattered. However, these materials are blown away with dust eliminating air such as air CA which is jetted to the space in front of the light incident face from the front end of the jetting tube 40 in the vicinity of the light incident face 21 which is in the outside of the image field of the camera 20, so that they will not reach at least the light incident face 21. Accordingly, fames or scattered tissue will not stick to the light incident face 21 which prevents the picked up images of the laser light irradiated area from becoming obscure. The air may be preferably used as jetting air for eliminating the dust on the light incident face 21. Another air may be used even it has such a clearness that it does not make the images obscure, but it is harmful.

Although a structure in which the camera 20 is integral with the handpiece 1 is adopted in the above-mentioned embodiment, in accordance with the present invention only the light incident face of the lens and the like may be integral with the handpiece so that optical transmitting means such as optical fiber is provided, which guides the light transmitted through the light incident face to the outside of the handpiece and the base end of the optical transmitting means is connected to a camera 20 which is separate from the handpiece (not shown). If the camera 20 is made integrally with the handpiece 1, the size of the camera 20 is limited. In latter case, there is an advantage that such a limitation is omitted.

Now, other accompanying forms of the present invention will be described.

Although a structure for supplying air and water for cooling is adopted in the afore-mentioned embodiment, these means may be omitted in accordance with the invention. In particular, although the air supply path and water supply path are common downstream of the handpiece 1, they may be separate from each other as shown in FIGS. 5 and 6.

Figure 5:
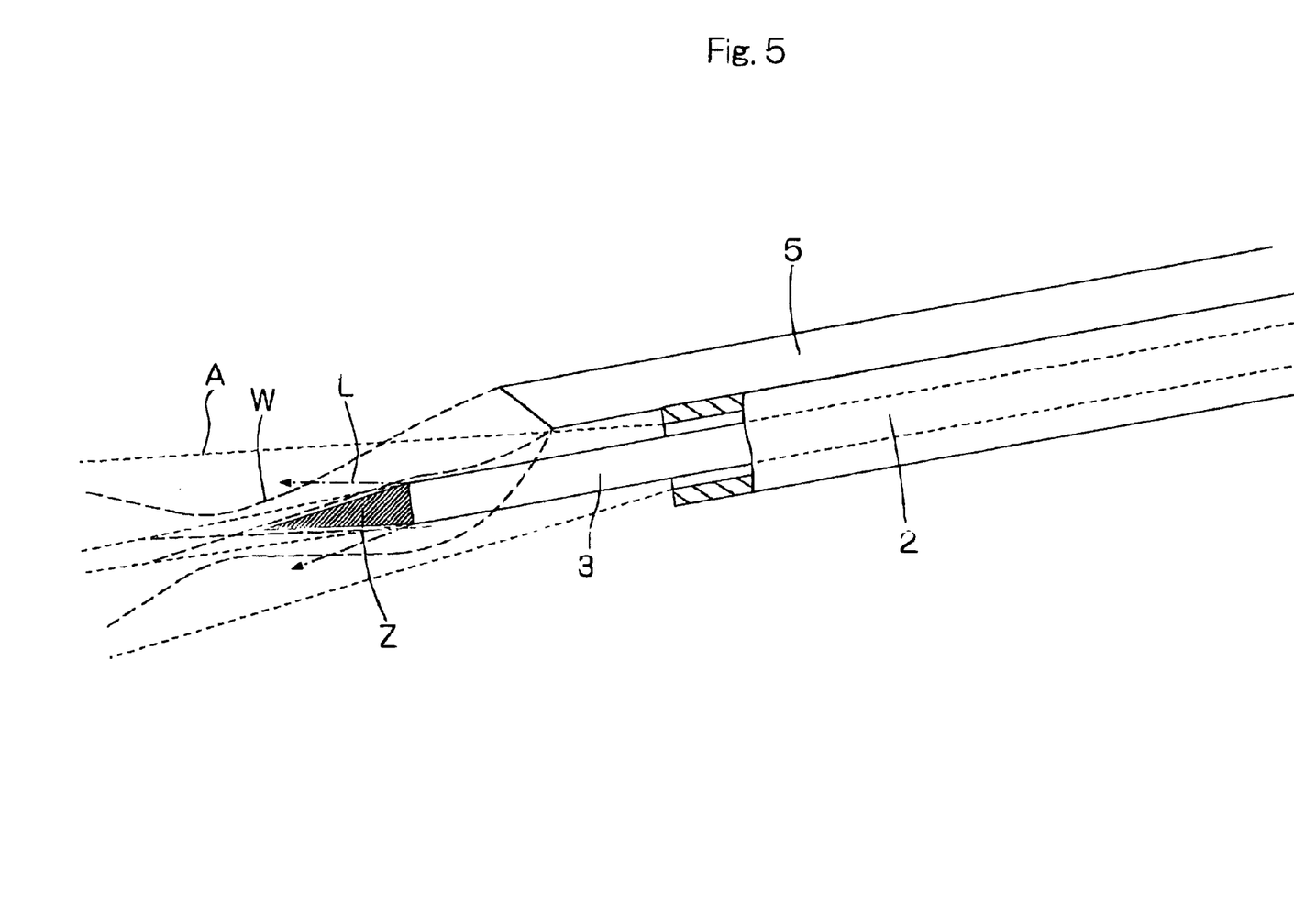
FIG. 5 is a view explaining the effective irradiated area with reference to the relation between the air and water flow.

In the form shown in FIG. 5, the handpiece 1 and guide tube 2 are provided with a water supply tube 5 made of a metal having a small diameter thereon and therealong. The water supply tube 5 is made integrally with the handpiece 1 and the guide tube 2 with bonding agent or welding. The water supply tube 5 is linked with the water supply tube 5A made of flexible plastics. Since the opening at the front end of the water supply tube 5 is located on the base side beyond the front end of the optical fiber 3 as shown in the drawing, water can be supplied forwardly from the periphery of the optical fiber in a substantially coaxial manner.

Figure 6:
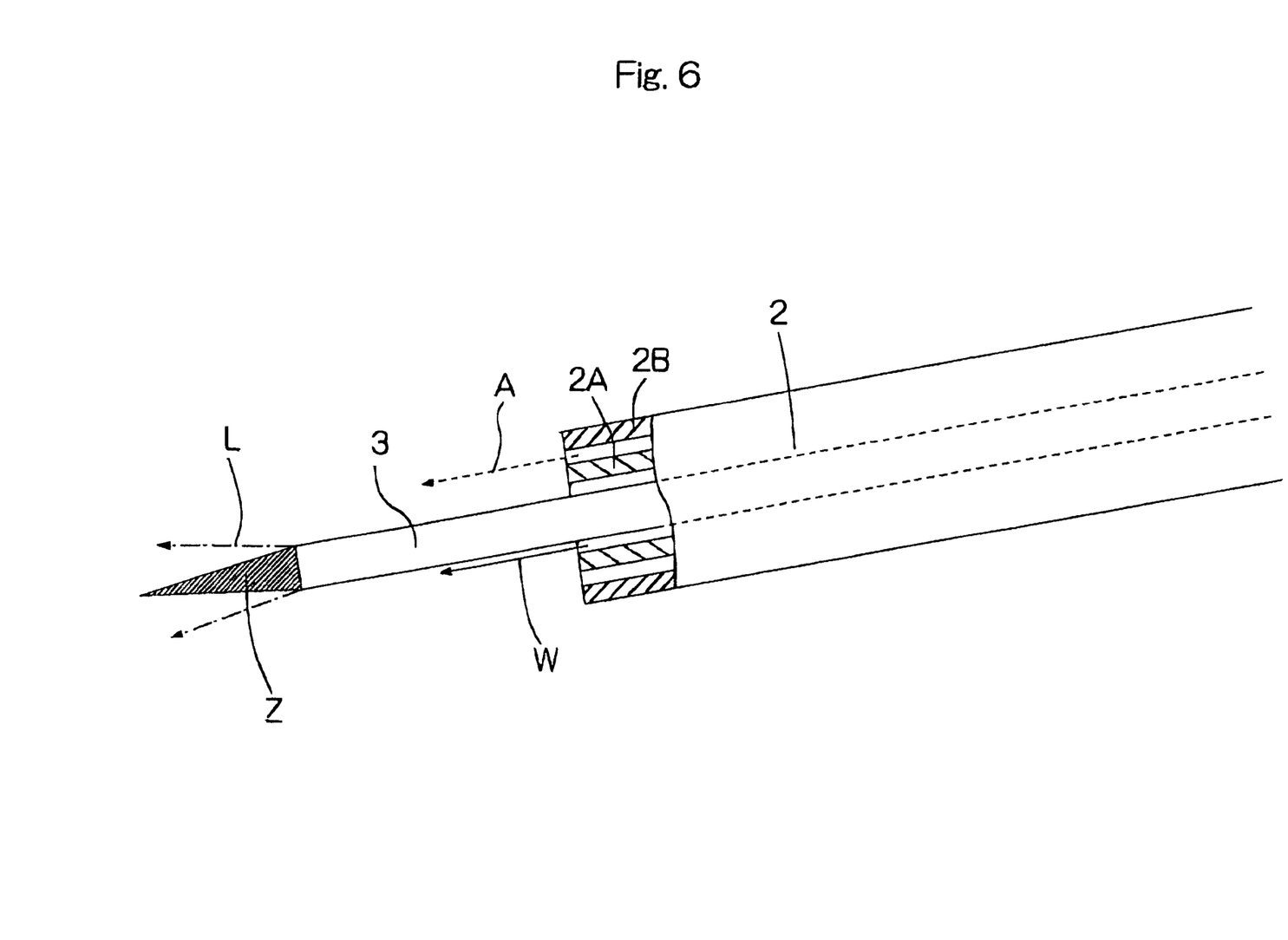
FIG. 6 is a partly taken away front view showing another example of the front end of the apparatus.

In the form shown in FIG. 6, a double coaxial tube, that is a guide tube 2 having inner and outer tubes 2A and 2B are provided. The optical fiber 3 is inserted into the inner tube 2A to form a water W supply path between the inner tube 2A and the optical fiber 3 and to form an air A supply path between the inner and outer tubes 2A and 2B.

The form of air and water supply for cooling in this embodiment will be observed in the air. When irradiation of the tissue with pulse laser light from the optical fiber and air supply is initiated simultaneously with supply of water W, the water W is carried by the flow of the air A and is caused to flow forwardly while it is moved around the front end of the optical fiber 3 as shown in FIG. 5. Part of the water W is atomized into mist in the course of flow. As shown in the drawings, the water W exhibits contracted flow in front of the front face of the optical fiber 3 and is diffused upstream of the contracted flow. The water W and air A will hardly flow into the effective irradiated area Z.

Accordingly, when the tissue M is irradiated with pulse laser light L for conducting incision, vaporization or solidification of the tissue M while the front end of the optical fiber 3 is close to the tissue M so that the tissue M surface is located within the effective irradiated area as shown in FIG. 4, the area of the tissue M surface which intersects with the effective irradiated area Z is not cooled by the water M and the laser light is not absorbed by water M and this area is irradiated with the laser light. Since the air A has the fastest flow rate in the center of the irradiation of the pulse laser light L and the flow of the air A accompanies the water W around the area of the tissue surface so that the water is replaced with flowing new water W. As a result, cooling is constantly effected around the area of the tissue M surface so that the temperature around the above-mentioned area of the tissue M surface will not be elevated.

The effect could be estimated from a result of the measurement of the temperature of the tissue by means of infrared ray camera when the actual tissue was irradiated with pulse lamer light L while changing the distance between the optical fiber 3 and the tissue.

The laser light having a wave length of 0.7 to 1.7 μm may be preferably used for, for example, dental applications. The laser light is preferably Nd:YAG laser light. The pulse laser light has preferable width of one pulse of 100 ms (mm sec) or less, energy of 30 mJ or more per one pulse and a repetition rate of 50 pps per one pulse. In the range of these conditions, it is possible to conduct hemostasis, incision, and evaporation of the soft tissue; hemostasis, sterilization and drainage of the gingiva; treatment of the infected root canal; removal and cleaning of tartar; cutting and drilling of the enamelum; butting and drilling of dentinum; bonding of crowns to each other, fixing of the metal implant screw by welding.

Selective removal of the caries portion of the tooth can be only achieved by using Nd:YAG laser light.

Figure 7:
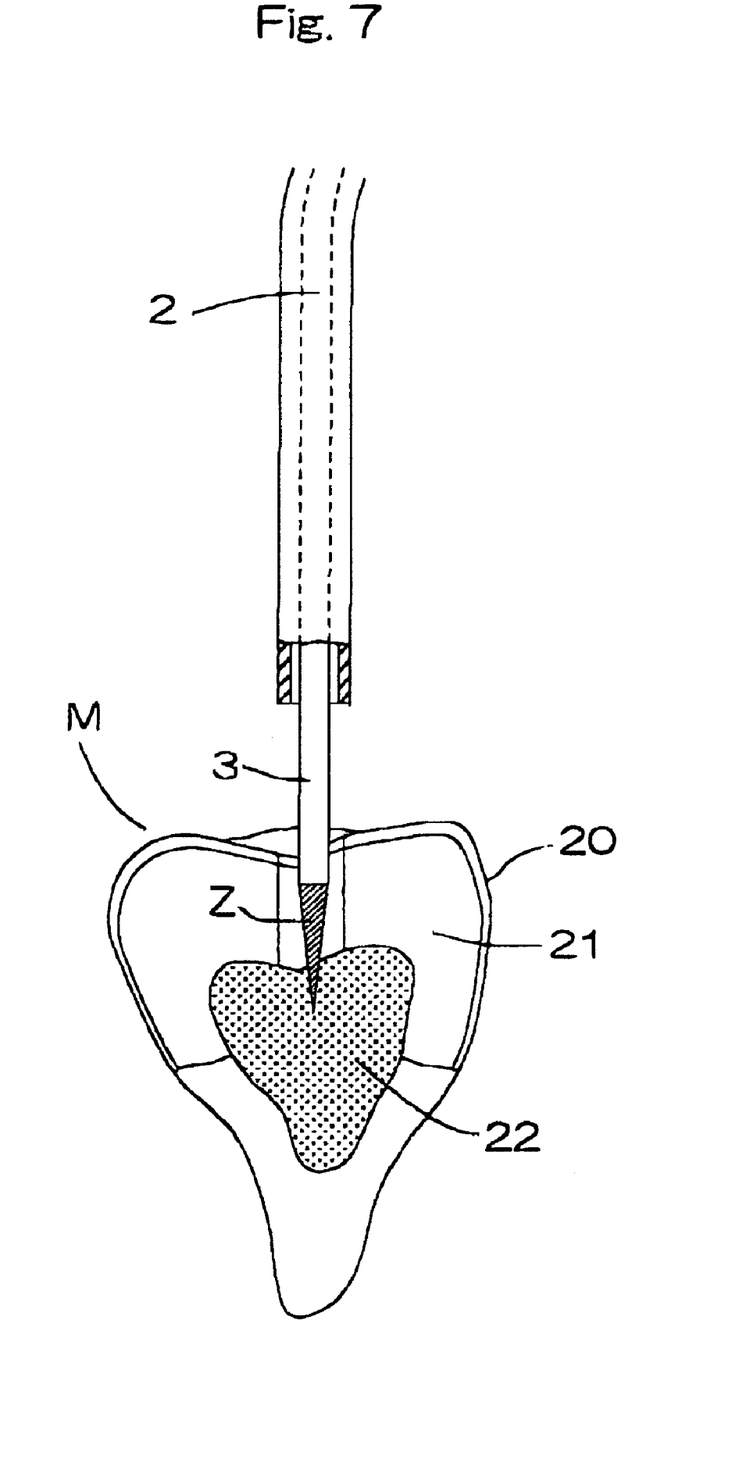
FIG. 7 is an explanatory view of the treatment on a tooth.

The treatment by removing the caries portion which has advanced from the enamelum 20 of the tooth M, cutting the dentinum 21 to remove the caries which has advanced through the dentinum 21 to the pulpa dentis 22 and by conducting root canal treatment in the pulpa dentis is shown in FIG. 7. Even if the pulpa dentis 22 is irradiated with the pulse laser light, the patient hardly feel pains.

In the present invention, a light guide chip which transmits the laser light to the front end of the optical fiber may be connected or placed. The front face of the optical fiber 3 may be in contact with the surface of the tissue M or is separated therefrom depending upon the kind of the treatment. Supplying of air and water makes the cooling effect upon the laser light irradiated position remarkably higher. Supplying of air will eliminate the incised or cut tissue, or evaporated or solidified material for reforming new tissue. Only air supplying or only water supplying may be conducted. Liquid such as alcohol may be used in lieu of water.

Water may be intermittently supplied in the process of supplying water. The water supply path may be opened or closed by means of the handpiece or foot switch for connecting intermittent water supply. Since the amount of the required water to be supplied is slight, the water may be supplied at a low rate such as one droplet from the front end of the water supply for 0.2 to 10 seconds.

If water flows from the front end of the water supply tube at a rate of one droplet per five seconds, only air is supplied for four seconds and air and water is supplied for one second while 5 pulses of the laser light are emitted per second.

As mentioned above, the present invention provides a medical laser light irradiating apparatus which enables operators as well as third persons to observe the treatment in a precise manner on treatment.

What is claimed is:

1. A laser light irradiating apparatus which uses laser light from laser light supply means for treatment, comprising:

an optical fiber for emitting from its front end the laser light which is incident upon the rear end thereof from said laser light supply means;

a handpiece for holding said optical fiber;

a light incident face which is made integrally with said handpiece so that it faces at least a laser light irradiated area;

imaging means for imaging of at least said laser light irradiated area based upon the light which is received through the light incident face;

display means for displaying a result of imaging from said imaging means;

jetting means for jetting a gas to an area in front of said light incident face; and a jetting switch interlocked with a laser light irradiating switch for continued jetting of gas at least during the irradiation of said laser light.

2. A laser light irradiating apparatus as defined in claim 1 in which said light incident face and imaging means comprise a camera which is integral with said handpiece.

3. A laser light irradiating apparatus which uses laser light from laser light supply means for treatment, comprising:

an optical fiber for emitting from its front end the laser light which is incident upon the rear end thereof from said laser light supply means;

a handpiece for holding said optical fiber;

a light incident face which is made integrally with said handpiece so that it faces at least a laser light irradiated area;

imaging means for imaging of at least said laser light irradiated area based upon the light which is received through the light incident face;

display means for displaying a result of imaging from said imaging means; and jetting means for jetting a gas to an area in front of said light incident face in which said light incident face and imaging means comprise a camera which is integral with said handpiece and said camera is movable with respect to said handpiece in a longitudinal direction thereof.

4. A laser light irradiating apparatus which uses laser light from laser light supply means for treatment, comprising:

an optical fiber for emitting from its front end the laser light which is incident upon the rear end thereof from said laser light supply means;

a handpiece for holding said optical fiber;

a light incident face which is made integrally with said handpiece so that it faces at least a laser light irradiated area;

imaging means for imaging of at least said laser light irradiated area based upon the light which is received through the light incident face;

display means for displaying a result of imaging from said imaging means;

jetting means for jetting a gas to an area in front of said light incident face in which said light incident face and imaging means comprise a camera which is integral with said handpiece and said camera is movable with respect to said handpiece in a longitudinal direction thereof; and mounting means for mounting said movable camera.

5. A laser light irradiating apparatus as defined in any one of claims 1 to 3 in which there is provided at least one of gas supply means for blowing gas into a space in front of the front end of said optical fiber and water supply means for supply water to the front end of said optical fiber; said laser light, said gas and said water are emitted to at least the laser light irradiated area.

6. A laser light irradiating apparatus as defined in any one of claims 1 to 4 and further including means for transmitting said result of imaging to other display via a communication network.

7. A laser light irradiating apparatus as defined in claim 1, wherein the area in front of said light incident face is away from a space in front of the front end of said optical fiber.

* * * * *